United States Patent

Merkel et al.

Patent Number: 6,054,258
Date of Patent: Apr. 25, 2000

[54] PHOTOGRAPHIC ELEMENTS CONTAINING HIGH-BOILING ESTERS

[75] Inventors: Paul B. Merkel, Victor; Ronald E. Leone, Rochester, both of N.Y.

[73] Assignee: Eastman Kodak Company, Rochester, N.Y.

[21] Appl. No.: 09/103,929

[22] Filed: Jun. 24, 1998

[51] Int. Cl.[7] .................................................. G03C 7/388
[52] U.S. Cl. ........................ 430/546; 430/570; 430/638
[58] Field of Search ..................... 430/570, 638, 430/546

[56] References Cited

FOREIGN PATENT DOCUMENTS 823327   2/1998   European Pat. Off. .

*Primary Examiner*—Janet Baxter
*Assistant Examiner*—Amanda C. Walke
*Attorney, Agent, or Firm*—Arthur E. Kluegel

[57] ABSTRACT

The invention disclosed is a photographic element comprising a support bearing at least one silver halide emulsion and at least one high-boiling solvent of structure I, below:

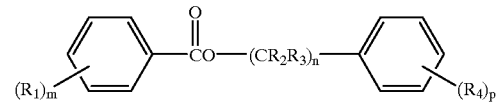

wherein:

m is 0, 1 or 2;

each $R_1$ is an individually selected alkyl group with up to four carbon atoms;

n is 2 to 5;

each $R_2$ and $R_3$ may be the same or different and is individually selected from hydrogen or an alkyl group with up to four carbon atoms;

p is 0 to 3;

each $R_4$ is independently a methyl or ethyl group; and the sum of the number of carbon atoms in each $R_1$ plus each $R_2$ plus each $R_3$ plus each $R_4$ taken together is three to seven.

19 Claims, No Drawings

PHOTOGRAPHIC ELEMENTS CONTAINING HIGH-BOILING ESTERS

FIELD OF THE INVENTION

This invention relates to a photographic element comprising a support bearing at least one silver halide emulsion and at least one high-boiling phenalkyl ester of benzoic acid or of an alkyl substituted benzoic acid.

BACKGROUND OF THE INVENTION

In a silver halide photographic element or material, a silver image is formed from silver halide following exposure and development. Silver halide photographic elements can comprise additional coated chemical components such as filter dyes and antifoggants that improve performance. Such components are often coated together with high-boiling organic solvents as small dispersion particles. The high-boiling solvents not only may aid in the dispersion and coating of beneficial components but also may improve properties or performance of such components.

In a silver halide color photographic element or material, a color image is formed when the element is given an imagewise exposure to light and then subjected to a color development process. In the color development process silver halide is reduced to silver as a function of exposure by a color developing agent, which is oxidized and then reacts with coupler to form dye. In most color photographic elements the coupler or couplers are coated in the element in the form of small dispersion droplets. Couplers are commonly dispersed and coated together with one or more high-boiling organic solvents, often referred to as coupler solvents. The high-boiling solvents may aid in dispersion preparation and coating and may beneficially alter the properties of couplers or of the dyes formed therefrom. For example, the proper choice of a high-boiling coupler solvent can increase coupler activity or improve dye thermal or light stability.

Many photographic elements or materials contain, in addition to imaging couplers, image-modifying couplers that release a photographically useful group from the coupling site upon reaction with oxidized color developer. Such image-modifying couplers are also commonly and adventitiously dispersed and coated together with one or more high-boiling solvents. In color photographic elements UV absorbing dyes, filter dyes, interlayer scavengers, antihalation dyes, antifoggants, stabilizers and other chemical components are also commonly dispersed and coated together with one or more high-boiling organic solvents.

It is usually desirable that a high-boiling solvent or coupler solvent remain in the layer in which it is coated and not wander into other layers or into processing solutions. Such wandering can produce unexpected or detrimental effects in a layer in which the high-boiling solvent was coated or in other layers of a multilayer photographic element. High-boiling solvents of low water solubility (e.g., less than about 6 mg/L) usually have adequate resistance to undesirable wandering. High-boiling solvents with a reasonably high degree of polarity are also desirable to aid in the dissolution and the dispersion of somewhat polar photographic chemicals, such as couplers or dyes. Solvents of high polarity can also provide improved dye hues. In addition, it is desirable that high-boiling solvents have reasonably low viscosity (less than about 500 centipoise). Low viscosity can aid in dispersion preparation and can result in smaller dispersion particles. Small dispersion particles can enhance coupler activity, reduce light scattering and can enhance dye-covering power.

There are numerous references to high-boiling solvents in the photographic art. A variety of types of high-boiling solvents are disclosed in Research Disclosure, December 1989, Item 308119, p 993, in U.S. Pat. Nos. 4,731,320, 4,900,655 and 5,451,492 and in European Patent 232,770. Ester type high-boiling solvents are disclosed in U.S. Pat. Nos. 4,080,209 and 4,873,182 and in British patent 2,217,470. None of these references discloses the structures or the advantageous use of the high-boiling solvents of the present invention. The high-boiling solvent 2-phenethylbenzoate, which while outside the scope of this invention may represent the closest prior art, is disclosed in photographic elements in U.S. Pat. Nos. 5,372,922, 5,594,047 and 5,618,657. Syntheses of high-boiling solvents of this invention are described in Chem. Lett. 4, 625 (1992), 3, 515 (1994) and 2, 141 (1995), but utilization in a photographic element is not disclosed.

There has been a need for high-boiling organic solvents that provide good dye hue but which will not diffuse from photographic layers to a significant extent during processing. These solvents must have low water solubility, low viscosity and moderate-to-high polarity. It is difficult to identify the structural features that lead to high-boiling solvents that satisfy these requirements. Furthermore, there has been a need to identify high-boiling solvents which are safe and in themselves are environmentally benign and whose decomposition products are environmentally benign.

SUMMARY OF THE INVENTION

This invention provides a photographic element, comprising a support bearing at least one silver halide emulsion and at least one high-boiling solvent of structure I, below:

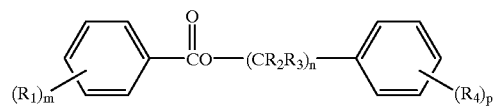

wherein:

m is 0, 1 or 2;

each $R_1$ is an individually selected alkyl group with up to four carbon atoms;

n is 2 to 5;

each $R_2$ and $R_3$ may be the same or different and is individually selected from hydrogen or an alkyl group with up to four carbon atoms;

p is 0 to 3;

each $R_4$ is independently a methyl or ethyl group; and the sum of the number of carbon atoms in each $R_1$ plus each $R_2$ plus each $R_3$ plus each $R_4$ taken together is three to seven.

The photographic elements of this invention provide high-boiling organic solvents that provide good dye hue but which will not diffuse from photographic layers to a significant extent during processing.

DETAILED DESCRIPTION OF THE INVENTION

This invention relates to a photographic element, comprising a support bearing at least one silver halide emulsion and at least one high-boiling solvent of structure I, below:

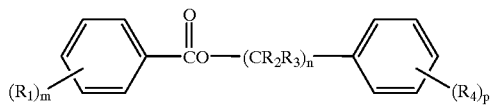

wherein:

m is 0, 1 or 2;

each $R_1$ is an individually selected alkyl group with up to four carbon atoms;

n is 2 to 5;

each $R_2$ and $R_3$ may be the same or different and is individually selected from hydrogen or an alkyl group with up to four carbon atoms;

p is 0 to 3;

each $R_4$ is independently a methyl or ethyl group; and the sum of the number of carbon atoms in each $R_1$ plus each $R_2$ plus each $R_3$ plus each $R_4$ taken together is three to seven.

In one useful embodiment m is 0. In another useful embodiment m is 1 and $R_1$ is a methyl group. In a preferred embodiment n is 3 and each $R_2$ and $R_3$ is hydrogen. In another preferred embodiment p is 0. In another useful embodiment the total number of carbon atoms in each $R_1$, each $R_2$, each $R_3$ and $R_4$ taken together is three to five. In a preferred embodiment the water solubility of the high-boiling solvent of structure I is less than 6 mg/L at 25° C. In another useful embodiment the high-boiling solvent of structure I has a viscosity of less than 500 centipoise and preferably less than 300 centipoise at 25° C. The logarithm of the ocatanol-water partition coefficient, also referred to as log P, of a substance provides a measure of water insolubility. The higher the log P of a substance, the lower is its water solubility. Log P values may be calculated using the program MEDCHEM, constructed by the Medicinal Chemistry Project at Pamona College of Clairmont Calif. A further discussion of log P values is provided in chapters four and five of "Exploring QSAR", C. Hansch and A. Leo, American Chemical Society, Washington, D.C., 1995. Useful coupler solvents of this invention will have log P values of approximately 4.5 or greater as calculated using version 3.54 of MEDCHEM.

The high-boiling phenalkyl esters of benzoic acid and substituted benzoic acids of this invention were designed to have log P values of at least 4.5 and to have low water solubility. The low water solubility of the high-boiling solvents of this invention provides the advantages of reduced wash out on processing of the photographic elements of this invention and reduced wandering of the high-boiling solvents within the photographic elements of this invention. Excessive wash out can lead to undesirable environmental consequences and to undesirable seasoning effects in processing solutions. Excessive wandering can lead to detrimental photographic effects within the layer in which the high-boiling solvent was coated or in other layers of a multilayer photographic element. The high-boiling solvents of this invention and their decomposition products are also expected to have lower undesirable biological effects than some high-boiling solvents currently used in the art, such as dibutyl phthalate.

The high-boiling solvents of this invention were also designed to have reasonably high polarity and polarizability. High polarity and polarizability can aid in dissolving a dispersing high-polarity photographic addenda such as couplers and dyes. High polarity/polarizability can also provide desirable bathochromic structured to avoid high viscosity.

Branching and maintaining low molecular weight help to provide reasonably low solvent viscosity. The low-moderate viscosities of the high-boiling solvents of this invention facilitate the preparation of dispersions having small particle sizes. This can offer advantages such as higher coupler activity and increased dye covering power.

The high-boiling phenalkyl benzoate esters of this invention may be utilized by dissolving one or more coupler, dye or other photographic addendum in them by heating, and then dispersing the solution as small particles in aqueous solutions of gelatin and surfactant via milling or homogenization. Removable auxiliary organic solvents such as ethyl acetate or cyclohexanone man, also be used in the preparation of such dispersions to facilitate the dissolution of the coupler, dye or addendum in the organic phase. Useful weight ratios of coupler, dye or addendum to high-boiling solvent range from about 1:0.1 to 1:8.0, with 1:0.3 to 1:2.0 being typical.

Useful coated levels of the high-boiling organic solvents of this invention range from about 0.02 to about 5.00 g/sq.m, or more typically from 0.05 to 3.00 g/sq.m.

The high-boiling phenalkyl esters of this invention may be codispersed with couplers, dyes, stabilizers, interlayer scavengers, antifoggants and other addenda in the photographic elements of this invention. Couplers codispersed with the high-boiling solvents of this invention may form cyan, magenta, yellow or black dyes or may be so-called universal couplers as further detailed below. Couplers codispersed with the high-boiling solvents of this invention may be 4-equivalent couplers or 2-equivalent couplers that release a coupling-off group. As also detailed below, such 2-equivalent couplers may release a photographically useful coupling-off group, such as an development inhibitor group, as released from a so-called DIR coupler. Dyes that may be codispersed with the high-boiling solvents of this invention include filter dyes, density correction dyes and sensitizing dyes and may be of any hue.

The high-boiling solvents of this invention may be utilized in black and white or color photographic elements, which may be negative working or positive working photographic elements. Furthermore, the photographic elements of this invention may contain a variety of types of silver halide emulsions, as elaborated below. Specifically contemplated is the use of the high-boiling solvents of this invention in photographic elements comprising one or more tabular grain silver halide emulsions. The high-boiling solvents of this invention may be coated on a variety of supports, including supports comprising magnetic recording layers.

The high-boiling phenalkyl esters of this invention may also be utilized in blends with other types of high-boiling organic solvents including aryl phosphates (e.g. tritolyl phosphate), alkyl phosphates (e.g. trioctyl phosphate), mixed aryl alkyl phosphates (e.g. diphenyl 2-ethylhexyl phosphate), aryl, alkyl or mixed aryl alkyl phosphonates, phosphine oxides (e.g. trioctylphosphine oxide), esters or aromatic acids (e.g. dibutyl phthalate, octyl benzoate, or benzyl salicylate), esters of aliphatic acids (e.g. acetyl tributyl citrate or dibutyl sebecate), alcohols (e.g. oleyl alcohol), phenols (e.g. p-dodecylphenol), carbonamides (e.g. N,N-dibutyldodecanamide or N-butylacetanalide), sulfoxides (e.g. bis(2-ethylhexyl)sulfoxide), sulfonamides (e.g. N,N-dibutyl-p-toluenesulfonamide) or hydrocarbons (e.g. dodecylbenzene). The high-boiling solvents of this invention may also be blended with polymers or loaded into polymeric latex dispersions for coating in a photographic element.

Examples of high-boiling organic solvents of this invention include, but are not limited to, A1-A1 6, below:

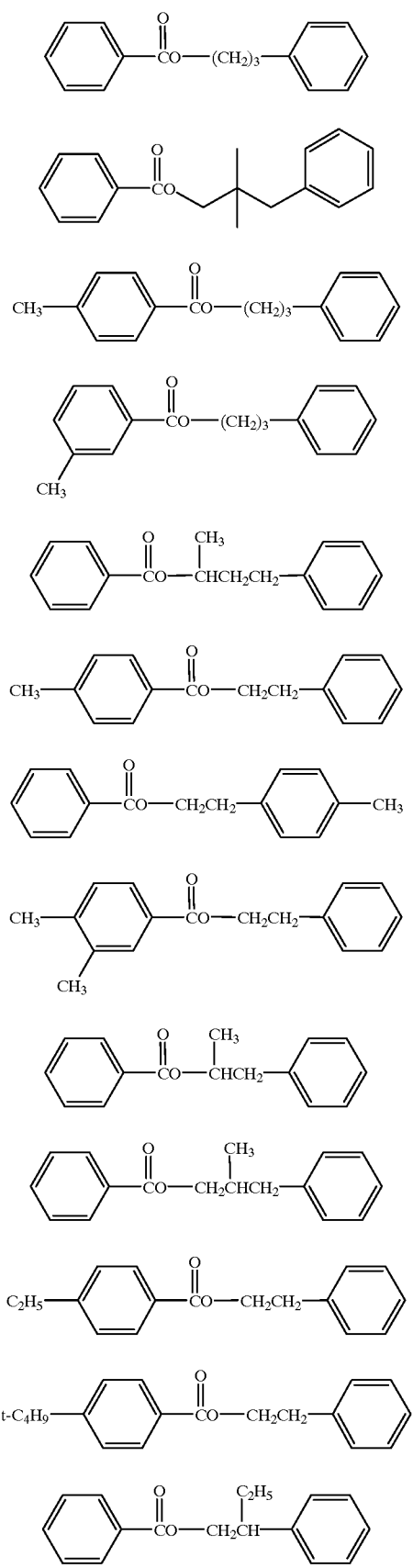

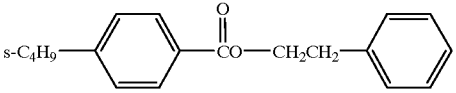

The high-boiling ester solvents of this invention may be synthesized by methods known in the art. An acid chloride of benzoic acid or of a substituted benzoic acid may be heated together with an equimolar amount of a phenalkyl alcohol in the presence of an aprotic base such as triethyl amine. The reaction between the acid chloride and the alcohol to form the desired ester proceeds nearly to completion. The ester may be washed with water to remove any residual acid chloride, acid or dissolved amine hydrochloride. The high-boiling ester may then be purified by distillation under vacuum. Synthesis of the high-boiling solvents of the invention may also be carried out as described in Chem. Lett. 4, 625 (1992), 3, 515 (1994) and 2, 141 (1995).

Unless otherwise specifically stated, the term substituted or substituent means any group or atom other than hydrogen bonded to the remainder of a molecule. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenox)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-prrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4(2,4-di-t-pentylphenoxy)butyl] carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoylox-, and cyclohexylcarbonyloxy; amine, such as phenylanilino, 2-chloroanilino, diethylamine, dodecylamine; irnino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure,* November 1992, Item 34390 published by Kenneth Mason Publications, Ltd., Dudley Annex, 12a North Street, Emsworth, Hampshire PO10 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure,* June 1994, Item 36230, provides suitable embodiments.

In the following discussion of suitable materials for use in the emulsions and elements of this invention, reference will be made to *Research Disclosure,* September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure,* Item No. 36544 referenced above, is updated in the September 1996 *Research Disclosure,* Item No. 38957. Certain desirable photographic elements and processing steps, including those useful in conjunction with color reflective prints, are described in *Research Disclosure,* Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006,755A and 2,017,704A, the disclosures of which are incorporated herein by reference.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. No. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0422 595; EPO 0428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. No. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328.818; 5,336,591; 5,338,654; 5,358,835; 5,358,838; 5,360,713; 5,362,617; 5,382,506; 5,389,504; 5,399,474;. 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632,345; 3,928,041; 3,958,993 and 3,961,959. Typically such couplers are cyclic carbonyl containing compounds that form colorless products on reaction with an oxidized color-developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color-developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530 272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention materials may be used in association with materials that release Photographically Useful Groups (PUGS) that accelerate or otherwise: modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784 may be useful. Also contemplated is use of the compositions in association with nucleating agents, development accelerators or their precursors (UK Patent 2,097,140; UK. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonarnidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photogaphic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch that produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, meraptothiazoles, mercaptotriazoles. mercaptooxadiazoles, mercaptodiazoles, mercaptooxathiazoles, telleuroterazoles or benzisodiazoles. In a preferred embodiment, the inhibitor moiety or group is selected from the following formulas:

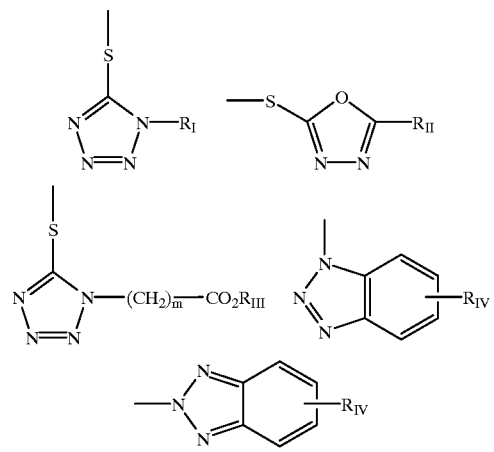

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features described above. It is typical that the timing group is of one of the formulas:

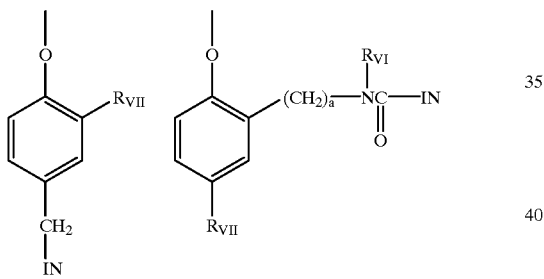

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkali and phenyl groups. The oxygen atom of each timing group is bonded to the coupling-off position of the respective coupler moiety of the DIAR.

The fining or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

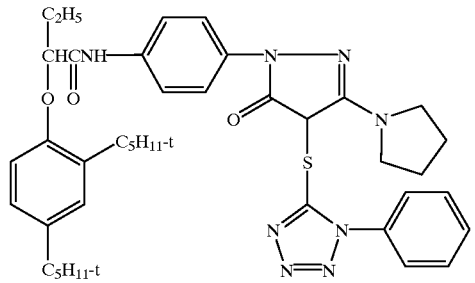

D1

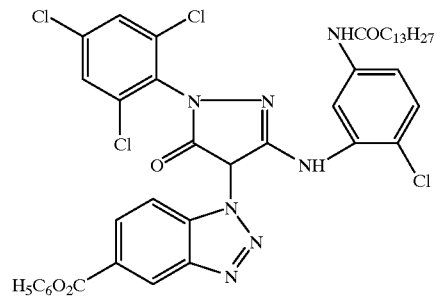

D2

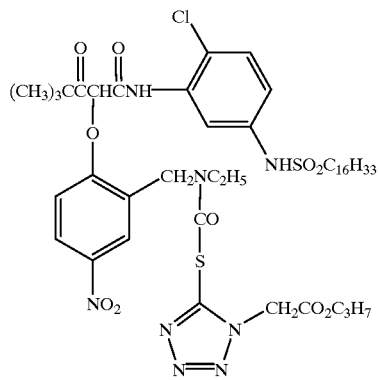

D3

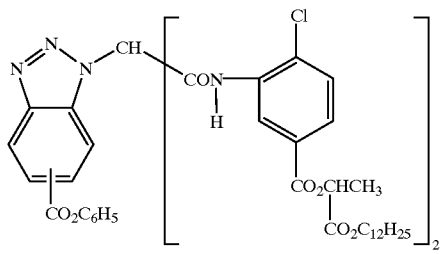

D4

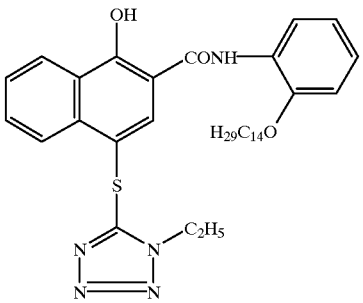

D5

D6
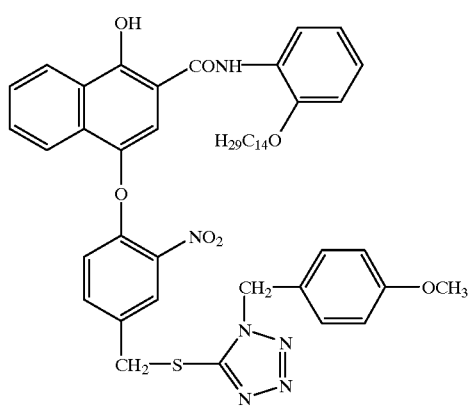
D7
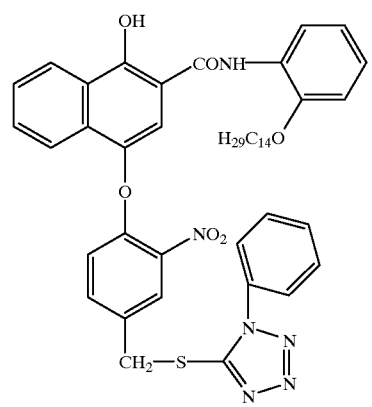
D8
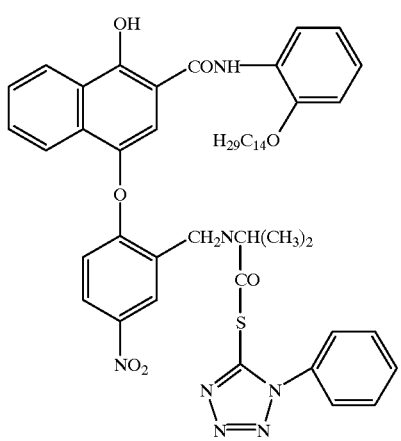
D9
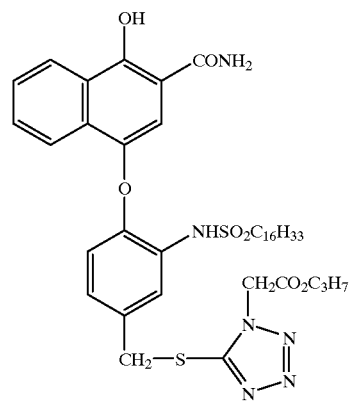
D10
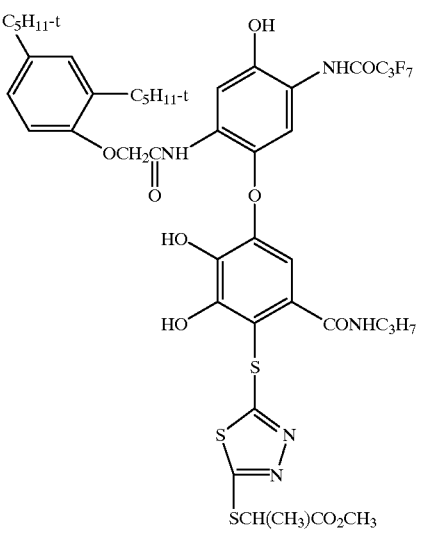
D11
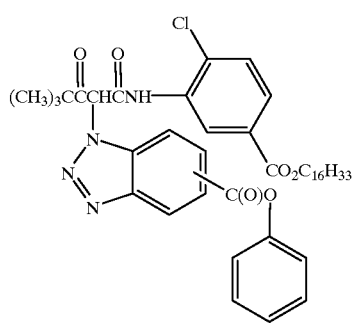
D12
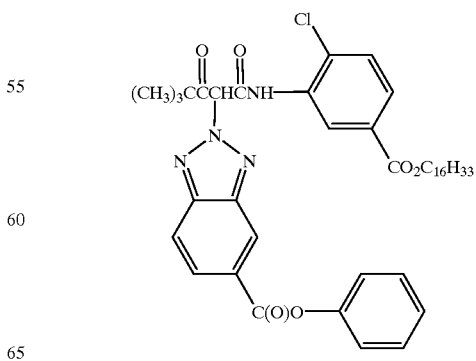

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339);, with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078, 230; 90-079,336; 90-079,337; 90-079,338; 90-079,690; 90-079,691; 90-080,487; 90-080,488; 90-080,489; 90-080, 490; 90-080,491; 90-080,492; 90-080,494; 90-085,928; 90-086,669; 90-086,670; 90-087,360; 90-087,361; 90-087, 362; 90-087,363; 90-087,364; 90-088,097; 90-093,662; 90-093,663; 90-093,664; 90-093,665; 90-093,666; 90-093, 668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, 1. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, So vinski et al U.S. Pat. No. 4,656,122, Piggin et al U.S. Pat. Nos. 5,061,616 and 5,061, 609, Tsaur et al U.S. Pat. Nos. 5,147,771, '772, '773, 5,171,659 and 5,252,453, Black et al 5,219,720 and 5,334, 495, Delton U.S. Pat. Nos. 5,310,644, 5,372,927 and 5,460, 934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713, 323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271, 858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320, 938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color-developing agent to reduce developable silver halide and oxidize the color-developing agent. Oxidized color-developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and may be processed, for example, in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak- C-41), color print (Kodak RA-4), or reversal (Kodak E-6) process.

Preferred color developing agents are p-phenylenediamines such as:

4-amino-N,N-diethylaniline hydrochloride,
4-amino-3-methyl-N,N-diethylaniline hydrochloride,
4-amino-3-methyl-N-ethyl-N-(2-methanesulfonamidoethyl)aniline sesquisulfate hydrate,
4-amino-3-methyl-N-ethyl-N-(2-hydroxyethyl)aniline sulfate,
4-amino-3-(2-methanesulfonamidoethyl)-N,N-diethylaniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the patents and other publications referred to in this specification are incorporated herein by reference.

EXAMPLE 1

Comparison of Water Solubility, Polarity and other Physical Properties of Conventional High-Boiling Solvents and High-Boiling Solvents of this Invention As noted earlier, high-boiling solvents are desired that have low water solubility and low-to-moderate viscosity and that provide suitably bathochromic dye hues, i.e. hues of suitably long wavelengths. In this example, these properties are evaluated for comparison high-boiling solvents known in the art and for high-boiling solvents of this invention. Results are summarized in Table I. Structures of the comparative high-boiling solvents are provided after Table I.

Water solubilities were obtained from plots of light scattering at 500 nm of dispersions of the high-boiling solvent in water versus concentration. The light scattering density goes to zero at the solubility limit, when dispersions of high-boiling solvent are diluted. Values of log P calculated using MEDCHEM version 3.54 are also given in Table I and serve as rough indicators of water solubility. Viscosities reported in Table I were measured using a Brookfield cone/plate viscometer. Solvents of high polarity and/or polarizability are often needed to provide suitably bathochromic hues for the types of dyes commonly encountered in color photographic materials. Dye C1, whose structure is provided after Table I, is representative of such dyes. The visible absorption maxima (Lambda max) values for C1, measured with a Perkin Elmer Lambda 2S spectrophotometer, are provided in Table I as measure of solvent polarity/polarizability.

TABLE I

| High-Boiling Solvent | Water Solubility (mg/L) | log P | Viscosity (centipoise) | Lambda max of Dye C1 (nm) |
|---|---|---|---|---|
| B1 (Comparison) | 9.4 | 4.69 | 17 | 674 |
| B2 (Comparison) | 0.8 | 5.98 | 9 | 658 |
| B3 (Comparison) | 2.6 | 5.68 | 6 | 661 |
| B4 (Comparison) | 10.0 | 4.06 | 14 | 674 |
| A1 (Invention) | 5.5 | 4.59 | 15 | 673 |
| A2 (Invention) | 2.5 | 5.39 | 99 | 668 |
| A3 (Invention) | 3.5 | 5.09 | 22 | 670 |

B1 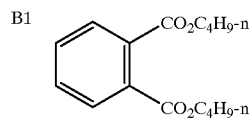

B2 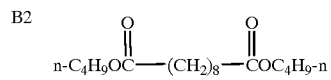

B3 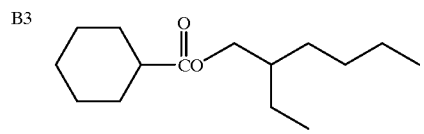

B4 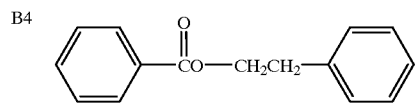

C1 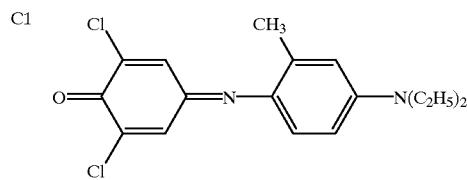

Comparative solvent B1 in Table I, dibutyl phthalate, is commonly used in many photographic materials. A major disadvantage of this solvent is its high water solubility of 9.4 mg/L. This high water solubility can allow wandering and wash out of B1, which can have deleterious effects on the photographic materials and on processing solutions. Comparative solvents B2 and B3 have higher log P values and lower water solubilities. However, B2 and B3 have reduced polarity/polarizability relative to B1 and consequently give much less bathochromic dye hues. The Lambda max values of the representative dye C1 are only 658 nm and 661 nm in B2 and B3, respectively, versus 674 nm in B1. High-boiling solvent B4, like B1, yields a suitably bathochromic hue for dye C1, but also like B1, solvent B4 has an excessively high water solubility of 10 mg/L. In contrast the high-boiling solvents A1, A2 and A3 of this invention all have water solubilities below 6 mg/L and yet provide bathochromic hues for dye C1 with lambda max values relatively close to those of B1 and B4. Thus only the high-boiling solvents of this invention provide the combination of suitably low water solubility and suitably high polarity/polarizability to provide desirable bathochromic dye hues. All of the high-boiling solvents in Table I, including A1, A2 and A3 of this invention, provide suitably low viscosities.

EXAMPLE 2

Simple Photographic Elements of this Invention

For this example, Coupler Y-1 (structure below) was dispersed and coated with comparative high-boiling solvent B1 and with high-boiling solvent A3 of this invention. The dispersions were prepared by adding an oil phase containing a 1:1:3 weight ratio of Y-1:high-boiling solvent: ethyl acetate to an aqueous phase containing gelatin and the dispersion agent ALKANOL XC (mixed isomers of triisopropyl-2-naphthalene sulfonic acid, sodium salt, DuPont) in a 10:1 weight ratio. The mixture was then passed through a colloid mill to disperse the oil in the aqueous phase as small particles. On coating, the ethyl acetate auxiliary solvent evaporates. The coupler dispersions were coated together with a silver iodobromide (3.5% iodide) emulsion on a transparent support. The coating structure is shown in Table II with laydowns in g/sq.m. given in parentheses.

TABLE II

Overcoat: Gelatin (2.69)
Bis(vinylsulfonyl)methane Hardener (0.129)
A Coupler Y-1 (0.978) & High-Boiling Solvent B1 (0.978) Comp.
or B Coupler Y-1 (0.978) & High-Boiling Solvent A2 (0.978) Inv.
0.7 μm Silver Iodobromide Emulsion (0.775 Ag)
Gelatin (3.77)
Cellulose Acetate Butyrate Support After hardening, samples of each of the films in Table II were given a sensitometric white light exposure and processed using the KODAK FLEXICOLOR C-41 procedure described in Table III. Measurements of status M blue density versus exposure were made for each processed film strip, and photographic contrast (gamma) was determined from the slopes of such plots. The blue gamma values from the films in Table II are compared in Table IV. High gamma values, a measure of color-forming efficiency, are generally desirable. The gamma value of 1.40 obtained with solvent A3 of this invention in coating B is similar to the gamma values of 1.48 obtained from comparative solvent B1 in coating A. Spectra of the yellow dye produced from Y-1 on development were measured at a blue density of about 1.0 using a Perkin Elmer Lambda 2S spectrophotometer. Lambda max values so obtained are also reported in Table IV and are similar with B1 and A3. Finally, the amount of wash out of high-boiling solvent B1 or A3 from films A or B, respectively, was measured after washing for 10 minutes in 38° C. water. Percent wash out of each high-boiling solvent is also reported in Table IV. Here the advantage of solvent A3 of this invention is evident, since it shows a significant reduction in wash out relative to comparative commercial solvent B1.

TABLE III

C41 Processing Solutions and Conditions

| Solution | Process Time | Agitation Gas |
| --- | --- | --- |
| C-41 Developer | 2'00" | Nitrogen |
| Stop Bath | 30" | Nitrogen |
| Wash | 2'00" | None |
| Bleach | 3'00" | Air |
| Wash | 3'00" | None |
| Fix | 4'00" | Nitrogen |
| Wash | 3'00" | None |
| Wetting Agent Bath | 30" | None |

Process temperature 37.8° C.

TABLE IV

| Coating | High-Boiling Solvent | Blue Gamma | Lambda max (nm) | % Washout 20 min 38° C. |
| --- | --- | --- | --- | --- |
| A | B1 (Comparative) | 1.48 | 449 | 6.2 |
| B | A3 (Invention) | 1.40 | 449 | 4.0 |

EXAMPLE 3

A Multilayer Photographic Element of this Invention

For this example, a multilayer color negative film containing high-boiling organic solvents A1, A2 and A3 of this invention is described. The multilayer film structure utilized in this example is shown schematically in Table V. Structures of components not provided previously are given immediately following Table V. Component laydowns are provided in units of g/sq.m. unless otherwise indicated. This composition may also be coated on a support, such as polyethylene naphthalate, containing a magnetic recording layer. After exposure this film may be processed using KODAK FLEXICOLOR C-41 processing chemistry.

TABLE V

Multilayer Film Structure

| | | |
| --- | --- | --- |
| 1 | Overcoat & UV Layer: | Matte Beads |
| | | UV Absorbers UV-1 (0.108), UV-2 (0.108) & S-1 (0.151) |
| | | Silver Bromide Lippmann Emulsion (0.215 Ag) |
| | | Gelatin (1.237) |
| | | Bis(vinylsulfonyl)methane Hardener (1.75% of Total Gelatin) |

TABLE V-continued

Multilayer Film Structure

| | | |
|---|---|---|
| 2 | Fast Yellow Layer: | Y-1 (0.236) Yellow Dye-Forming Coupler & A3 (0.118) |
| | | IR-1 (0.076) DIR Coupler & A3 (0.038) |
| | | B-1 (0.0054) BARC & S-3 (0.0070) |
| | | Silver Iodobromide Emulsion (0.377 Ag), |
| | Blue Sensitive | 4.1 mole % Iodide T-Grain (2.9 × 0.12 μm) |
| | | Silver Iodobromide Emulsion (0.108 Ag), |
| | Blue Sensitive | 4.1 mole % Iodide T-Grain (1.9 × 0.14 μm) |
| | | Gelatin (0.807) |
| 3 | Slow Yellow Layer: | Y-1 (1.076) & A3 (0.538) |
| | | IR-1 (0.076) & A3 (0.038) |
| | | B-1 (0.022) & S-3 (0.0028) |
| | | CC-1 (0.032) & A1 (0.064) |
| | | IR-4 (0.032) & A1 (0.064) |
| | Blue Sensitive | Silver Iodobromide Emulsion (0.398 Ag), |
| | | 4.1 mole % Iodide T-Grain (1.9 × 0.14 μm) |
| | Blue Sensitive | Silver Iodobromide Emulsion (0.269 Ag), |
| | | 1.3 mole % Iodide T-Grain (0.54 × 0.08 μm) |
| | Blue Sensitive | Silver Iodobromide Emulsion (0.247 Ag), |
| | | 1.5 mole % Iodide T-Grain (0.77 × 0.14 μm) |
| | | Gelatin (1.872) |
| 4 | Yellow Filter Layer: | R-1 (0.086) & A1 (0.139) & ST-2 (0.012) |
| | | YD-2 Filter Dye (0.054) |
| | | Gelatin (0.646) |
| 5 | Fast Magenta Layer: | M-1 (0.075) Magenta Dye-Forming Coupler & S-1 (0.068) |
| | | & ST-1 (0.0075), Addendum, R-2 (0.009) |
| | | MM-1 (0.054) Masking Coupler & S-1 (0.108) |
| | | IR-2 (0.030) DIR Coupler & A1 (0.060) |
| | | B-1 (0.003) & S-3 (0.004) |
| | Green Sensitive | Silver Iodobromide Emulsion (0.484 Ag), |
| | | 4.0 mole % Iodide T-Grain (1.60 × 0.12 μm) |
| | | Gelatin (1.014) |
| 6 | Mid Magenta Layer: | M-1 (0.124) & S-1 (0.111) & ST-1 (0.012) |
| | | MM-1 (0.118) & S-1 (0.236), R-2 (0.015) |
| | | IR-3 (0.043) DIR Coupler & A1 (0.043) |
| | Green Sensitive | Silver Iodobromide Emulsion (0.247 Ag), |
| | | 4.0 mole % Iodide T-Grain (1.20 × 0.11 μm) |
| | Green Sensitive | Silver Iodobromide Emulsion (0.247 Ag), |
| | | 4.0 mole % Iodide T-Grain (1.00 × 0.12 μm) |
| | | Gelatin (1.216) |
| 7 | Slow Magenta Layer: | M-1 (0.269) & S-1 (0.242) & ST-1 (0.027) |
| | | MM-1 (0.086) & S-1 (0.172) |
| | | IR-3 (0.011) & A1 (0.011) |
| | Green Sensitive | Silver Iodobromide Emulsion (0.34 Ag), |
| | | 3.5 mole % Iodide T-Grain (0.90 × 0.12 μm) |
| | Green Sensitive | Silver Iodobromide Emulsion (0.129 Ag), |
| | | 1.5 mole % Iodide T-Grain (0.50 × 0.08 μm) |
| | | Gelatin (1.076) |
| 8 | Interlayer: | R-1 (0.086) Interlayer Scavenger, A1 (0.139) |
| | | & ST-2 (0.012) |
| | | Gelatin (0.538) |
| 9 | Fast Cyan Layer: | CC-1 (0.183) Cyan Dye-Forming Coupler & A1 (0.210) |
| | | CM-1 (0.022) Masking Coupler |
| | | IR-4 (0.027) DIAR Coupler & A1 (0.054) |
| | Red Sensitive | Silver Iodobromide Emulsion (0.592 Ag), |
| | | 4.1 mole % Iodide T-Grain (1.7 × 0.12 μm) |
| | | Gelatin (0.915) |
| 10 | Mid Cyan Layer: | CC-1 (0.170) & A1 (0.190) |
| | | CM-1 (0.032) |
| | | B-1 (0.008) & S-3 (0.010) |
| | | IR-4 (0.019) & A1 (0.038) |
| | Red Sensitive | Silver Iodobromide Emulsion (0.194 Ag), |
| | | 4.1 mole % Iodide T-Grain (1.2 × 0.11 μm) |
| | Red Sensitive | Silver Iodobromide Emulsion (0.236 Ag), |
| | | 4.1 mole % Iodide T-Grain (0.91 × 0.11 μm) |
| | | Gelatin (1.076) |
| 11 | Slow Cyan Layer: | CC-1 (0.533) & A1 (0.560) |
| | | IR-4 (0.026) & A1 (0.052) |
| | | CM-1 (0.031) |
| | | B-1 (0.056) & S-3 (0.073) |
| | Red Sensitive | Silver Iodobromide Emulsion (0.463 Ag), |
| | | 1.5 mole % Iodide T-Grain (0.54 × 0.06 μm) |
| | Red Sensitive | Silver Iodobromide Emulsion (0.301 Ag), |
| | | 4.1 mole % Iodide T-Grain (0.53 × 0.12 μm) |
| | | Gelatin (1.679) |

TABLE V-continued

Multilayer Film Structure

| | | |
|---|---|---|
| 12 | Antihalation Layer: | Gray Silver (0.135) |
| | | UV-1 (0.075), UV-2 (0.030), S-1 (0.042), S-4 (0.015) |
| | | YD-1 (0.034), MD-1 (0.018) & A2 (0.018) |
| | | CD-1 (0.025) & A1 (0.125) |
| | | R-1 (0.161), A1 (0.261) & ST-2 (0.022) |
| | | Gelatin (2.044) |
| | Cellulose Triacetate Support | |

S-1

(CH$_3$—⟨phenyl⟩—O)$_3$—P=O mixed isomers

S-3 n-C$_{11}$H$_{23}$C(=O)—N(C$_2$H$_5$)$_2$

S-4

[cyclohexane-1,4-diyl bis(methylene) bis(2-ethylhexanoate); ester groups: OC(=O)CH(C$_2$H$_5$)C$_4$H$_9$-n]

S-5

(2-ethylhexyl—O)$_3$P=O

UV-1 n-C$_6$H$_{13}$—N(C$_6$H$_{13}$-n)—CH=CH—CH=CH—C(CN)$_2$ (—CN, —CN)

UV-2

CH$_3$O—⟨phenyl⟩—CH=C(CN)—C(=O)—O—C$_3$H$_7$-n

IR-2

[Benzotriazole derivative: benzotriazolyl—CH—(CONH—⟨2-Cl, 5-substituted phenyl⟩); phenyl substituent: CH$_3$—CH—(CO$_2$CHCO$_2$C$_{12}$H$_{25}$-n)$_2$; benzotriazole 5-CO$_2$—phenyl]

TABLE V-continued

Multilayer Film Structure

R-1

[Structure: 2,5-dihydroxybenzene with t-$C_8H_{17}$ substituents at 1 and 4 positions]

ST-2

[Structure: phenol with t-$C_4H_9$ groups at 2,6 positions and $CH_2CH_2CO_2C_{18}H_{37}$-n at 4 position]

YD-2

[Structure: furanone with n-$C_4H_9SO_2NH$-phenyl, CN, and furfurylidene substituents]

R-2

[Structure: dihydroxybenzene with $CH(CH_3)C_{16}H_{33}$-n and $HOSO_2$ substituents]

MM-1

[Structure: pyrazolone magenta coupler with 2,4,6-trichlorophenyl group, azo linkage to 3,4-dimethoxyphenyl, and NH-chlorophenyl-NHCOCHO(n-$H_{25}C_{12}$)-(3-t-$C_4H_9$-4-OH-phenyl) group]

TABLE V-continued

Multilayer Film Structure

IR-3, ST-1, M-1, CC-1 (chemical structures)

TABLE V-continued

Multilayer Film Structure

CM-1

[Chemical structure of CM-1: 1-hydroxy-naphthalene-2-carboxamide with -(CH$_2$)$_4$-O-phenyl bearing two t-C$_5$H$_{11}$ groups; 4-position linked via -O- to a phenyl-azo-naphthol with NHCOCH$_3$, and two SO$_3^-$·PYRH$^+$ groups]

IR-4

[Chemical structure of IR-4: 1-hydroxy-naphthalene-2-carboxamide-N-(2-(n-C$_{14}$H$_{29}$O)phenyl); 4-position -O- linked to 2-nitro-4-(CH$_2$-S-tetrazolyl)phenyl, tetrazole N-substituted with CH$_2$-(4-methoxyphenyl)]

B-1

[Chemical structure of B-1: 1-hydroxy-4-(SCH$_2$CH$_2$COOH)-naphthalene-2-carboxamide-N-(2-(n-C$_{12}$H$_{25}$O)-5-methylphenyl)]

MD-1

[Chemical structure of MD-1: 1-(2,4,6-trichlorophenyl)-pyrazolone with =N-arylimino (2-methyl-4-(N-ethyl-N-(2-hydroxyethyl)amino)phenyl) at 4-position; 3-NHCO-(3-(NHCOCH$_2$O-(2-t-C$_5$H$_{11}$-4-C$_5$H$_{11}$-t-phenyl))phenyl)]

TABLE V-continued

Multilayer Film Structure

CD-1
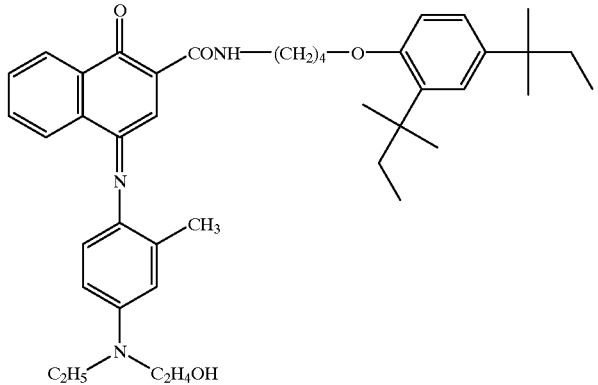

YD-1
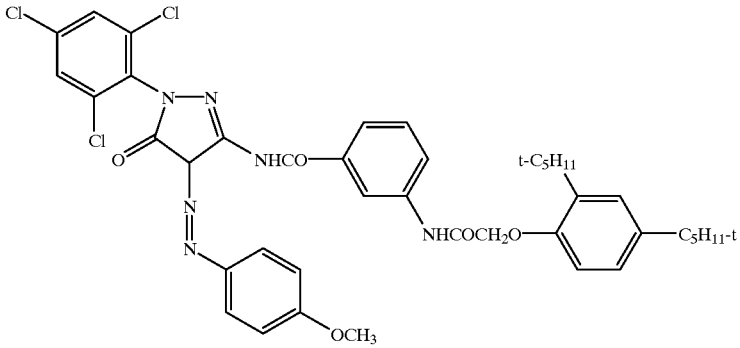

The preceding examples are set forth to illustrate specific embodiments of this invention and are not intended to limit the scope of the compositions, materials or methods of the invention. Additional embodiments and advantages within the scope of the claimed invention will be apparent to one skilled in the art.

The invention has been described in detail with particular reference to certain preferred embodiments thereof, but it will be understood that variations and modifications can be effected within the spirit and scope of the invention.

What is claimed is:

1. A photographic element, comprising a support bearing at least one silver halide emulsion and at least one high-boiling solvent of structure I, below:

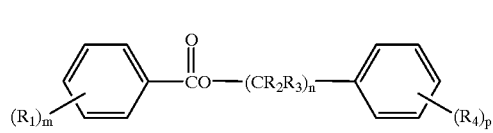

wherein:

$m$ is 0, 1 or 2;

each $R_1$ is an individually selected alkyl group with up to four carbon atoms;

$n$ is 2 to 5;

each $R_2$ and $R_3$ may be the same or different and is individually selected from hydrogen or an alkyl group with up to four carbon atoms;

$p$ is 0 to 3;

each $R_4$ is independently a methyl or ethyl group; and the sum of the number of carbon atoms in each $R_1$ plus each $(CR_2R_3)$ plus each $R_4$ taken together is three to seven.

2. A photographic element according to claim 1, wherein the water solubility of said high-boiling solvent is less than 6.0 mg/L at 25° C.

3. A photographic element according to claim 1, wherein the log P of said high-boiling solvent is at least 4.5.

4. A photographic element according to claim 1, wherein the viscosity of said high-boiling solvent at 25° C. is less than 500 centipoise.

5. A photographic element according to claim 4, wherein the viscosity at 25° C. is less than 300 centipoise.

6. A photographic element according to claim 1, wherein said high-boiling solvent is sufficiently polar to provide a spectral absorption maximum of at least 665 nm. for a solution of dye C1, below:

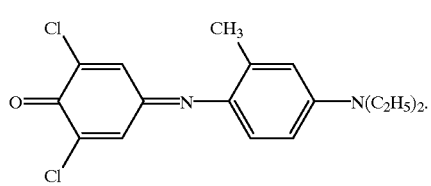

7. A photographic element according to claim 1, wherein m is 0.

8. A photographic element according to claim 1, wherein m is 1 and $R_1$ is a methyl group.

9. A photographic element according to claim 1, wherein n is 3 and each $R_2$ and $R_3$ is hydrogen.

10. A photographic element according to claim 1, wherein p is 0.

11. A photographic clement according to claim 1 wherein the number of carbon atoms in each $R_1$ plus each $(CR_2R_3)$ plus $R_4$ taken together is three to five.

12. A photographic element according to claim 1, wherein the high-boiling solvent is selected from the group consisting of:

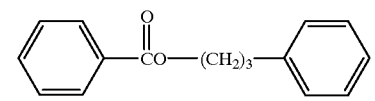
A1

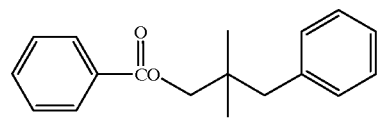
A2

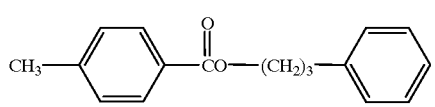
A3

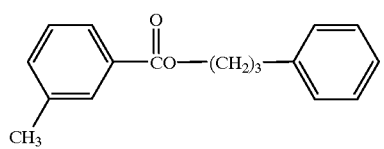
A4 and

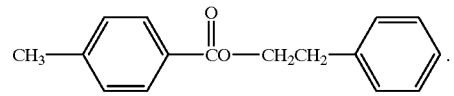
A6

13. A photographic element according to claim 1, wherein the high-boiling solvent is coated at a level between 0.02 and 5.00 g/sq m.

14. A photographic element according to claim 1, wherein the high-boiling solvent is co-dispersed with a cyan dye-forming coupler.

15. A photographic element according to claim 1, wherein the high-boiling solvent is codispersed with a magenta dye-forming coupler.

16. A photographic element according to claim 1, wherein the high-boiling solvent is codispersed with a yellow dye-forming coupler.

17. A photographic element according to claim 1, wherein the high-boiling solvent is codispersed with a dye.

18. A photographic element according to claim 1, wherein at least one of said silver halide emulsions is a tabular grain emulsion.

19. A photographic element according to claim 1, wherein said support comprises a magnetic recording layer.

* * * * *